United States Patent [19]

Miller

[11] Patent Number: 4,932,870
[45] Date of Patent: Jun. 12, 1990

[54] DENTAL POST AND METHOD FOR MAKING THE SAME

[75] Inventor: Alan N. Miller, New City, N.Y.

[73] Assignee: IPCO Corporation, White Plains, N.Y.

[21] Appl. No.: 233,679

[22] Filed: Aug. 18, 1988

[51] Int. Cl.$^5$ .............................................. A61C 5/08
[52] U.S. Cl. .................... 433/221; 433/225
[58] Field of Search .............. 433/221, 225, 220, 173; 29/160.6

[56] References Cited

U.S. PATENT DOCUMENTS

| | | | |
|---|---|---|---|
| 1,517,500 | 12/1924 | Fredericks | 433/221 |
| 2,536,669 | 1/1951 | Thau-Jensen | 433/221 |
| 4,185,383 | 1/1980 | Heimke et al. | 433/173 |
| 4,474,556 | 10/1984 | Ellis et al. | 433/173 |
| 4,729,736 | 3/1988 | Weissman | 433/221 |
| 4,767,332 | 8/1988 | Weissman | 433/225 |
| 4,820,159 | 4/1989 | Weissman | 433/225 |

FOREIGN PATENT DOCUMENTS 843972  7/1981  U.S.S.R. .............................. 433/220

*Primary Examiner*—Cary E. Stone
*Attorney, Agent, or Firm*—Helfgott & Karas

[57] ABSTRACT

A dental post for retaining a dental restoration onto a tooth stub and a method for making dental post. The dental post includes a cylindrical body portion and a head portion which extends outwardly from the body portion. The body portion is inserted in a bore in the tooth and secured therein by cement. To improve cement retaining capacity of the dental post, there are provided on the body portion non-continuous raised portions, spaced by wide open gaps to retain large segments of thick segments of cement. The overall portion of the gap area surface is greater than that of the land area surface.

19 Claims, 3 Drawing Sheets

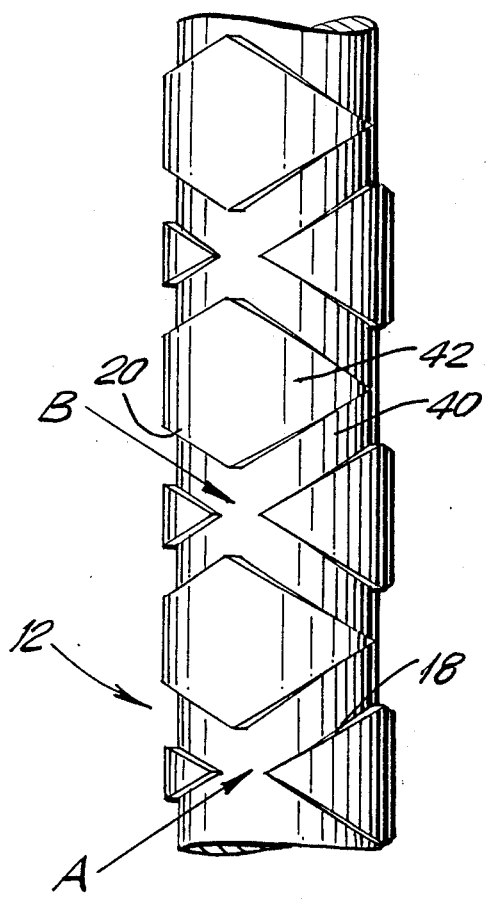
FIG.9
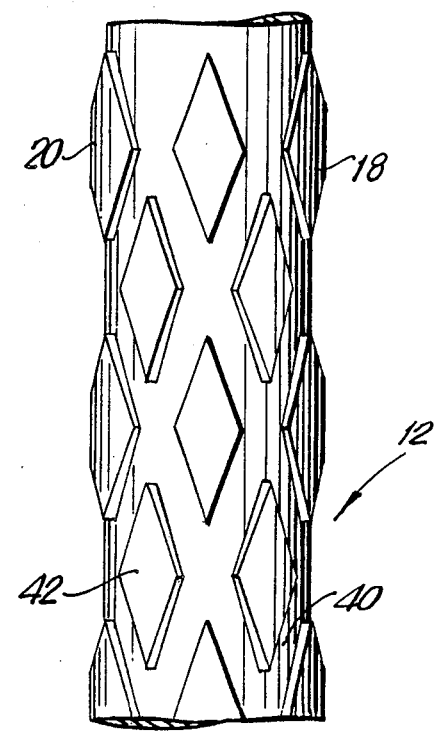
FIG.10
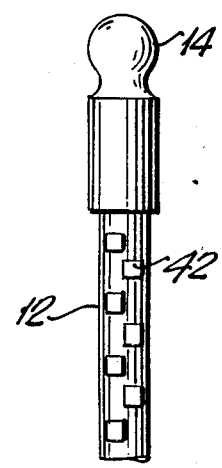
FIG.11
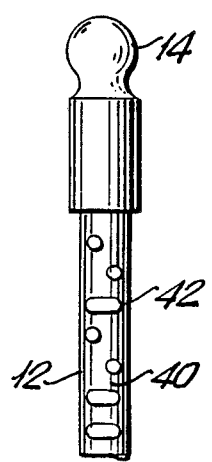
FIG.12
FIG.13
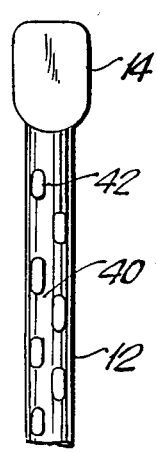
FIG.14

DENTAL POST AND METHOD FOR MAKING THE SAME

BACKGROUND OF THE INVENTION

The present invention pertains to a dental post for retaining a dental restoration onto a tooth stub and to a method for making dental posts.

In dental practice, it has been well known to utilize a dental post for retaining a dental restoration or prosthetic structure which is built onto the tooth stub of the broken tooth. Normally, the tooth stub is prepared by cutting it down and drilling in it a bore into which a dental post is inserted. The dental post which is retained in the bore by suitable dental cement is received in the bore so that its cylindrical body substantially fills the bore while its head portion extends upwardly from the surface of the tooth stub. Then, a dental core is formed on the head portion of the dental post, and the dental restoration is built up on the dental core.

Dental posts known in the art are provided with various means which aid in retention of the dental posts within the bores of the tooth stubs. On some posts, there has been provided an external thread which forms an additional surface area to retain cement. The external thread may be a spiral thread formed about the periphery of the substantially cylindrical body portion of the dental post. Retention means on the dental post may be also formed by helical flutes or grooves of a large pitch. The multiple helical grooves also provide an increased surface for the cement to enter and thus a better retention of the dental post in the bore of the tooth stub.

U.S. Pat. No. 2,536,669 discloses a dental post on the shank and the head of which are provided inclined grooves. The grooves are inclined in two opposite directions with respect to the longitudinal axis of the shank.

While prior art dental posts with different retention grooves as described hereinabove have generally been quite useful, there has been a need to provide dental posts with more substantial retention means which would further prevent accidental pulling or rotating out of the dental post after setting in the cement.

SUMMARY OF THE INVENTION

Accordingly, it is an object of the present invention to provide an improved dental post.

It is another object of this invention to provide a dental post with increased retention capacity in a tooth stub.

It is a further object of the present invention to provide a dental post which is easy and inexpensive to manufacture.

Yet another object of the invention to provide a dental post with venting means of enhanced capacity.

Still another object of the present invention is to provide a dental post with increased resistance to rotation of the post within the bore of the tooth stub.

Briefly, in accordance with the present invention, there is provided a dental post for retaining a dental restoration onto a prepared tooth stub. The dental post comprises an elongated body portion and a head portion. The body portion is provided with retention means for anchoring the body portion within a cement prepared bore in the tooth stub. The outer surface of the body portion is formed with a raised area portion and a groove area portion. The latter forms the cement containment means. The ratio between the groove area portion and the raised area portion is greater than 1:1 so that the groove area portion may hold and secure relatively large sections of thickened portions of the cement to significantly improve cement retention.

In an embodiment, the raised area portion is formed by lands spaced from each other by grooves or gaps which can be adjusted in size. The ratio between the groove area portion and the raised area portion may be in the ratio of 60 to 40.

In an embodiment, two crossing threads are formed on the outer surface of the body portion of the post, which then define the raised area portion and the groove area portion.

The pitch and the depth of the threads may be altered to adjust the ratio between the groove area portion and the raised area portion.

In another embodiment, lands spaced from each other by wide open gaps or grooves for retaining cement are provided on the outer surface of the body portion of the dental post. The lands may be round, oval, square, trapezoidal, or rectangular in shape. The lands may be arranged on the outer surface of the body portion in rows or at random.

In accordance with the method of the present invention, cross threads or lands on the outer surface of the body portion may be produced by casting.

In an embodiment, the cross threads can be formed by cold forming. The cross threads may be also formed by EDM-thread rolling dies or by cutters. The speed of the screw machine may be adjusted to alter the ratio between the groove area portion and the raised area portion.

The aforementioned objects, features and advantages of the invention, will, in part, be pointed out with particularity, and will, in part, become obvious from the following more detailed description of the invention, taken in conjunction with the accompanying drawings, which form an integral part thereof.

BRIEF DESCRIPTION OF THE DRAWING

In the drawing:

FIG. 9 is a partial side view of the dental post as seen from arrow 9 shown in FIG. 1;

FIG. 10 is a side view of the dental post similar to that of FIG. 9 but with the cross threads having a rhombic configuration;

FIG. 11 is a side view of the dental post of another embodiment;

FIG. 12 is a side view of the dental post of still another embodiment;

FIG. 13 is a side view of a further embodiment; and

FIG. 14 is a side view of the dental post of yet another embodiment of the invention.

DETAILED DESCRIPTION OF THE PREFERRED EMBODIMENT

Figure 1:
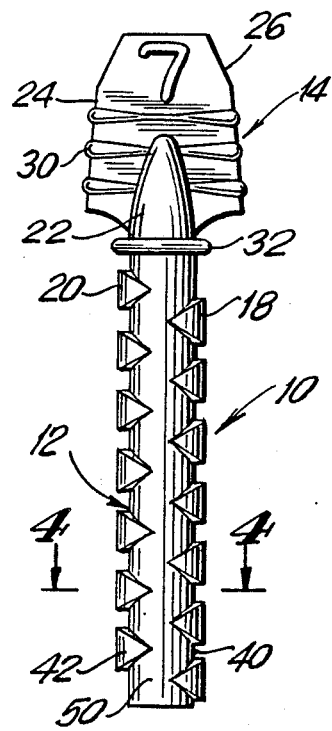
FIG. 1 is a side view of the dental post of a first embodiment of the invention.

Referring now to the drawings, FIGS. 1 to 7, 9 and 10 illustrate different embodiments of the dental post provided with cross threads. FIG. 1 shows a side view of a dental post generally denoted at 10 and including an elongated cylindrical body portion 12 and a head portion 14. Two helical threads 18 and 20 extending in opposite directions and crossing each other are formed about a peripheral surface of the body portion 12 as will be explained in detail below.

As seen in FIG. 1, the head portion 14 includes a substantially conical neck 22 which supports a flattened head 24 terminated with an upwardly tapering tip portion 26. A plurality of horizontal ribs 30 vertically spaced from each other are provided on the external surface of head portion 14. An annular collar 32 interconnects the neck 22 and the body portion 12 of the dental post. The structure of the head portion 14 formed as a flattened tang member is known and has been disclosed in U.S. Pat. No. 4,571,187.

As best seen in FIG. 9 which is a partial side view of the body portion 12 of FIGS. 1 to 7 turned by 90°, a first spiral thread designated at 18 extends in one direction indicated by arrow A whereas a second spiral thread 20 extends in the direction of arrow B which is opposite to that of thread 18. Grooves or depressions 40 between lands 42 formed by the cross threads 18 and 20 form the cement containing regions, the overall area of which constitutes by way of example 60% of the entire peripheral surface of the body portion 12 of the dental post while the remaining 40% to the peripheral surface of body portion 12 are taken by lands 42. The pitch of each thread 18, 20 as well as the depth of depressions 40, can be changed depending on requirements.

Figure 2:
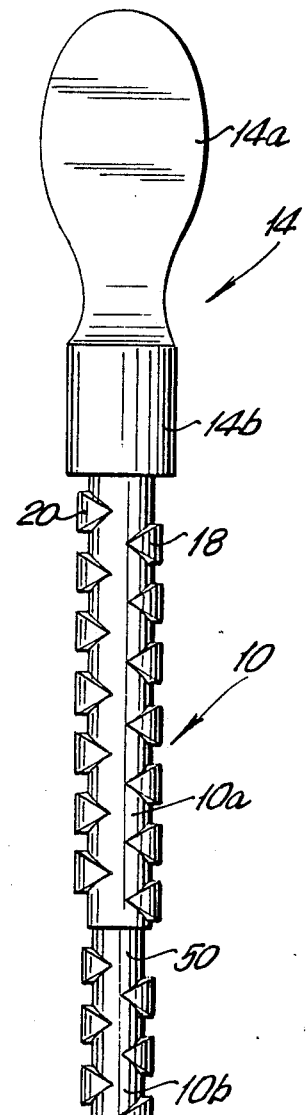
FIG. 2 is a side view of another embodiment of the dental post.
Figure 4:
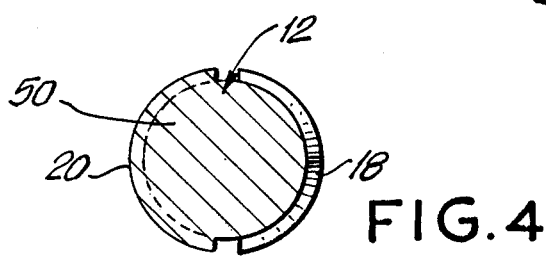
FIG. 4 is a sectional view taken along line 4—4 of FIG. 1.

FIG. 2 shows the embodiment of the dental post 10 with two cross threads 18,20 formed on its body portion 12 and the head portion 14, an upper portion 14a of which is sub- stantially oval and which is reduced in cross-section in the direction towards the body portion 12. The oval-shaped portion 14a of the head is adjoined with a substantially cylindrical lower portion 14b which merges into body portion 12 of the dental post. The body portion is stepped with the upper step 10a being of larger diameter than the lower step 10b. However, the same cross thread is on both steps. The cylindrical portion 14b forms yet a wider step but is unthreaded.

Figure 3:
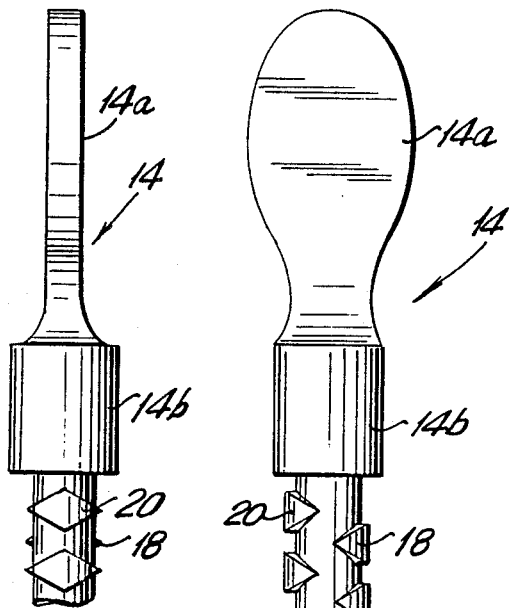
FIG. 3 is a partial side view of yet another embodiment.

In the embodiment of FIG. 3, the dental post with two cross-threads 18, 20 on body portion 12 thereof has a flattened head 14 which has one portion 14a of a reduced cross-section and another portion 14b of an enlarged cross-section.

Figure 5:
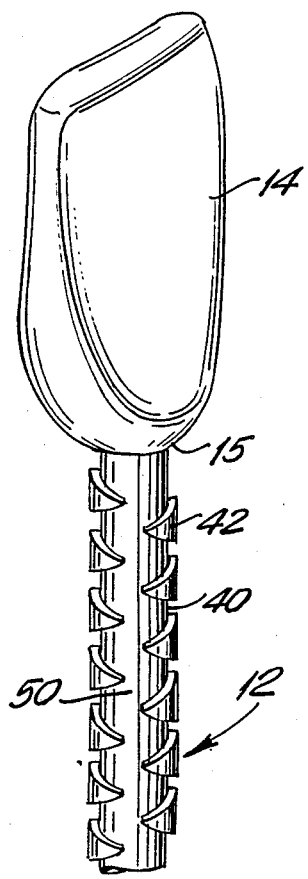
FIG. 5 is a perspective view of the dental post of still another embodiment.
Figure 6:
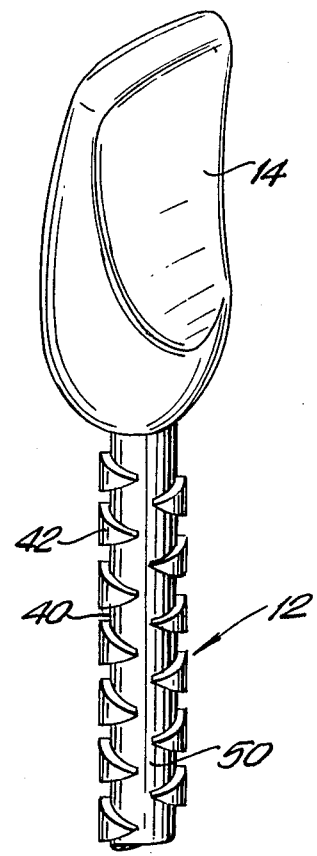
FIG. 6 is a perspective view of the dental post of FIG. 5 turned by 180°.

FIGS. 5 and 6 show the body portion with depressions 40 and lands 42 similar to the aforedescribed embodiments and the head portion 14 the shape of which conforms to the anatomical shape of the dental restoration which is to be supported on the dental post. An undercut 15 for retaining cement is formed at the transition between the head portion 14 and the body portion 12. Head portion 14 has no sharp edges and is wider than body portion 12 in the mesio-distal orientation and the labial-lingual orientation as well.

Figure 7:
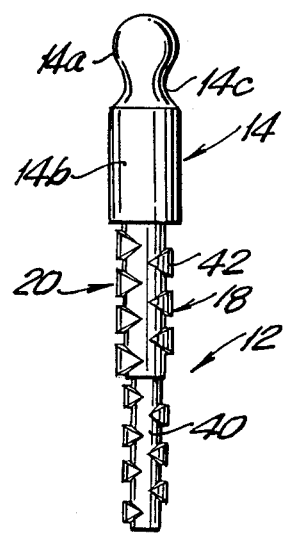
FIG. 7 is a side view of yet another modification of the dental post.

In the embodiment illustrated in FIG. 7, lands 42 which limit therebetween a larger surface of depressions or grooves 40 are also formed by two cross-threads 18 and 20 schematically shown in FIG. 7. The head portion 14 of the dental post in this embodiment includes a substantially cylindrical section 14b joining the stepped body portion 12 of the dental post and a substantially oval-shaped section 14a having a reduced diameter throat 14c of circular cross-section which is joined with the cylindrical section 14b.

In all the above-described embodiments the surface area occupied by depressions 40 is by about 20% greater than the overall surface area of lands 42. Cement adheres not only within the grooves or depressions 40, but is also provided about the entire periphery of the post and also provides a layer about the peripheral surfaces of lands 42. Effectively the layer of cement is continuous about the post periphery with thin layers about the lands and thicker layers in the grooves.

The spacing between lands 42 formed by two threads 18 and 20 crossing each other not only serves to retain a large continuous portion of cement but also provides a venting path 50 to allow air to escape along that path from the bore in the tooth stub as the dental post is inserted into that bore. The venting path 50 formed between lands 4 is made during the producing of the cross-threads, without requiring any additional operations.

As best seen FIG. 10, the pitch of threads 18 and 20 can be selected that substantially rhombic lands 42 may be formed, which are elongated in the direction of the axis of the body portion 12. Two approximately axial natural venting paths would result from the cross-threads of this embodiment.

As compared to conventional helically fluted dental posts or dental posts with an external spiral thread, in a dental post with two crossing threads, the width and depth of which can be altered, wide open spaces are formed between lands 42 in all the embodiments disclosed herein. These wide open spaces are capable of retaining large segments of the thicker part of the continuous layer of cement, which segments are wedged in between lands 42 and are interlocked there. The depth of grooves or depressions 40 form wide spaces sufficient to permit cement to enter into these grooves and be reliably held between the bore formed in the tooth stub and the outer surface of the dental post. The greater space of the cross-threads as opposed to conventional helical flutes ensures that larger segments of cement can be adhered to the surface of the dental post, which significantly improves cement retention of the post within the bore of the tooth stub. It has been found that it is such large segments of cement which aids in retention.

A further advantage of the two crossing threads on the outer surface of the dental post resides in that these threads form a reliable mechanism for preventing rotation of the dental post within the bore in each of the two opposite rotational directions. This increase in effective resistance to rotational torque aids in the retentive qualities of the post.

Yet another advantage of the cross threads is its use on a so-called burnout post. A burnout post is a temporary plastic post normally used during the casting of a permanent dental post. By using such cross threads on the burnout post the dental post will be cast in a like manner with wide open spaces between the lands.

Figure 8:
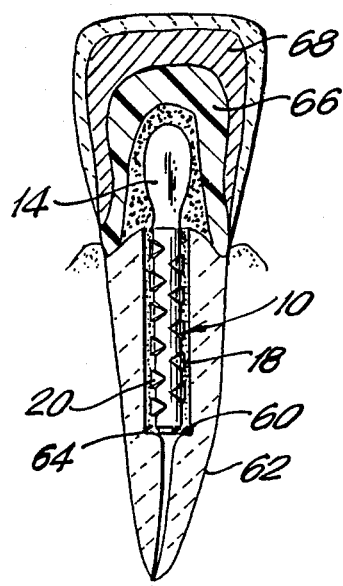
FIG. 8 is a sectional view through the tooth stub, showing the insertion of the dental post with the core and restoration built up on the dental post.

As shown in FIG. 8 the dental post 10 with cross threads 18 and 20 is inserted into a bore 60 formed in the tooth stub 62. A space 64 formed between the inner surface of bore 60 and the lands at the periphery of the post is filled with cement. The cement forms thicker segments in the wide open grooves formed by depressions 40 between lands 42 of the cross-threads on the dental post 10. This cement secures the dental post 10 in the tooth stub 62. A dental core 66 is then built up on the head portion 14 of the dental post, extending outwardly from tooth stub to support thereon the dental restoration 68.

The land portions need not only be formed by a cross thread arrangement. The land portions could be formed in other symmetrical or even non-symmetrical arrangements.

By way of example, FIG. 11 shows lands or raised portions 42 of substantially oval shape with their axes of elongation extending normal to the axis of elongation of the cylindrical body position 12.

As seen in FIG. 12 lands or protrusions 42 can be of substantially rectangular configuration and arranged on the outer surface of the body portion 12 in rows or at random spaced relationship with one another.

FIG. 13 shows the embodiment in which oval as well as round-shaped lands 42 are formed on the external surface of the body 12, which lands are spaced from each other so that wide open spaces or depressions 40 for cement retention are left therebetween.

FIG. 14 illustrates yet another embodiment of cement retention means and vent means formed by wide open spaces 40 remaining between lands 42 which are of substantially oval configuration with their axes of elongation extending along the axis of elongation of body portion 12.

The entire land portion is non-continuous in all the embodiments while the groove portion is formed to retain a large continuous portion of cement.

It is, of course, understandable that lands 42 can be of any suitable shape or configuration such as rhombic, trapezoidal, square, etc. and be arranged on the outer surface of the body portion in any suitable fashion as long as the ratio between the overall solid portion and the overall groove portion on the outer surface of the body portion of the dental post is less than 50 percent. For example, this ratio can be 3:2.

Cross threads on the dental posts of the embodiments of FIGS. 1–7, 9 and 10 can be produced on screw machines or by EDM-thread rolling dies, cold forming, casting or molding, or by cutters. The pitch and/or depth of each thread can be altered so that the groove portion of the outer surface of the body portion can be adjusted. Lands or raised portions 42 on the dental posts in the embodiments of FIGS. 11 to 14 are made, preferably by cast. When using the cross threads and forming on a screw machine, the post can be threaded by moving it axially in one direction through the screw machine and then axially reversing its direction through the screw machine for forming the opposing threads.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A dental post for retaining a dental restoration in secured position, the dental post being inserted in a bore of a tooth stub, which bore is to be filled with cement, the dental post comprising:
   an elongated substantially cylindrical body portion having an outer surface;
   a head portion extending from said body portion for projecting outwardly from the tooth stub to support thereon a dental restoration when said body portion is inserted into the bore of the tooth stub; and
   cement retention means formed on said outer surface;
   said outer surface including a raised area portion and a groove area portion which constitutes said cement retention means, wherein a ratio between said groove area portion and said raised area portion is greater than 50%,
   said raised portion and said groove area portion being formed by two threads provided on said outer surface and crossing each other,
   said each thread being open at each end thereof so that groove area portion being a continuous non-interrupted area to permit air to escape from the bore of the tooth stub when said body portion is cemented in said bore.

2. A dental post as in claim 1, wherein said ratio is 60 to 40.

3. A dental post of claim 1, wherein a pitch of each of said threads is adjustable to adjust said ratio between said groove area portion and said raised area portion.

4. A dental post of claim 1, wherein a depth of each thread is adjustable to adjust said ratio between said groove area portion and said raised area portion.

5. A dental post of claim 1, wherein said crossing threads form lands spaced from each other to enclose therebetween at least one vent to further assist air in escaping from the bore of the tooth stub when said body portion is cemented in said bore.

6. A dental post as in claim 5, wherein said lands are of substantially rhombic shape.

7. A dental post as in claim 5, wherein two vent paths extending approximately axially on said body portion are formed between said lands.

8. A dental post as in claim 1, wherein said head portion includes a flattened tang member.

9. A dental post as in claim 1, wherein said head portion is of substantially oval cross-section.

10. A dental post as in claim 1, wherein said head portion is flattened.

11. A dental post as in claim 1, wherein said head portion has a configuration corresponding to an anatomical shape of the dental restoration.

12. A dental post as in claim 1, wherein said body portion is stepped.

13. A method of making dental posts of the type having an elongated substantially cylindrical body portion and a head portion for supporting a dental restoration and extending outwardly from the body portion which is to be secured in a bore of a tooth stub by cement, the method comprising the steps of forming on an outer surface of the body portion two crossing threads each being open at each end thereof which form grooves for retaining cement, so that a continuous, non-interrupted groove area portion is formed on said outer surface and an overall groove area portion constitutes on said outer surface more than 50% of the surface.

14. A method as in claim 13, wherein a pitch of said crossing threads can be altered.

15. A method as in claim 13, wherein a depth of said crossing threads can be altered.

16. A method as in claim 13, wherein said crossing threads are formed by thread rolling.

17. A method as in claim 13, wherein said crossing threads are formed by casting.

18. A method as in claim 13, wherein said crossing threads are formed by cold forming.

19. A method as in claim 13, wherein said crossing threads are formed by cutters.

* * * * *